United States Patent
Yan et al.

(10) Patent No.: US 10,112,884 B2
(45) Date of Patent: Oct. 30, 2018

(54) ASYMMETRICAL HYDROGENATION REACTION OF KETONIC ACID COMPOUND

(71) Applicant: Zhejiang Jiuzhou Pharma science & technology Co., Ltd., Hangzhou (CN)

(72) Inventors: Pucha Yan, Taizhou (CN); Yuanqiang Li, Taizhou (CN); Daqing Che, Taizhou (CN); Xiangdong Zhang, Taizhou (CN); Kang Chen, Taizhou (CN); Yongliang Yan, Taizhou (CN)

( * ) Notice: Subject to any disclaimer, the term of this patent is extended or adjusted under 35 U.S.C. 154(b) by 0 days.

(21) Appl. No.: 15/508,933

(22) PCT Filed: Apr. 28, 2015

(86) PCT No.: PCT/CN2015/077660
§ 371 (c)(1),
(2) Date: Mar. 6, 2017

(87) PCT Pub. No.: WO2016/041351
PCT Pub. Date: Mar. 24, 2016

(65) Prior Publication Data
US 2017/0260119 A1 Sep. 14, 2017

(30) Foreign Application Priority Data
Sep. 15, 2014 (CN) .................. 2014 1 0468805

(51) Int. Cl.
| | |
|---|---|
| *C07C 51/367* | (2006.01) |
| *B01J 31/18* | (2006.01) |
| *B01J 31/24* | (2006.01) |
| *C07B 53/00* | (2006.01) |
| *C07F 9/58* | (2006.01) |
| *C07C 59/01* | (2006.01) |
| *C07C 59/11* | (2006.01) |

(Continued)

(52) U.S. Cl.
CPC .......... *C07C 51/367* (2013.01); *B01J 31/189* (2013.01); *B01J 31/1815* (2013.01); *B01J 31/2447* (2013.01); *C07B 53/00* (2013.01); *B01J 2231/643* (2013.01); *B01J 2531/0241* (2013.01); *B01J 2531/827* (2013.01); *C07B 2200/07* (2013.01); *C07C 59/01* (2013.01); *C07C 59/11* (2013.01); *C07C 59/48* (2013.01); *C07C 59/50* (2013.01); *C07C 59/56* (2013.01); *C07C 59/64* (2013.01); *C07C 2601/14* (2017.05); *C07F 9/58* (2013.01)

(58) Field of Classification Search
CPC ............... B01J 31/1815; B01J 31/2447; B01J 2231/643; B01J 2531/827; B01J 31/24; C07B 53/00; C07B 2200/07; C07C 51/367; C07C 2601/14; C07C 59/01; C07C 59/11; C07C 59/48; C07C 59/50; C07C 59/56; C07C 59/64; C07F 9/58
See application file for complete search history.

(56) References Cited

U.S. PATENT DOCUMENTS

| | | | |
|---|---|---|---|
| 8,962,839 B2 | 2/2015 | Zhou et al. | |
| 2013/0225822 A1* | 8/2013 | Zhou ................ | B01J 31/189 |
| | | | 546/22 |

FOREIGN PATENT DOCUMENTS

| | | |
|---|---|---|
| CN | 1112563 A | 11/1995 |
| CN | 1439643 A | 9/2003 |
| CN | 101671365 A | 3/2010 |

OTHER PUBLICATIONS

Himeda et al., "pH-Dependent Catalytic Activity and Chemoselectivity in Transfer Hydrogenation Catalyzed by Iridium Complex with 4,4'-Dihydroxy-2,2'-bipyridine," Chem. Eur. J. 2008, 14, 11076-11081 (Year: 2008).*

(Continued)

*Primary Examiner* — Pancham Bakshi
*Assistant Examiner* — Mark R Luderer

(57) ABSTRACT

The present invention relates to the technical field of organic chemistry, specifically an asymmetrical hydrogenation of an ∂-ketonic acid compound, the technical proposal being as shown by the following formula:

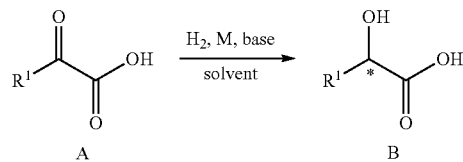

Wherein $R^1$ is a phenyl, a substituted phenyl, a naphthyl a substituted naphthyl, a $C_1$-$C_6$ alkyl or aralkyl, the substitute is a $C_1$-$C_6$ alkyl, a $C_1$-$C_6$ alkoxy, a halogen, the number of the substituents is 1-3.

M is a chiral spiro-pyridyl amido phosphine ligand iridium complex having the following structure,

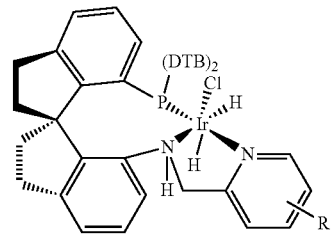

Wherein, R is hydrogen, 3-methyl, 4-$^t$Bu or 6-methyl

8 Claims, 2 Drawing Sheets

(51) Int. Cl.
    *C07C 59/48*     (2006.01)
    *C07C 59/50*     (2006.01)
    *C07C 59/56*     (2006.01)
    *C07C 59/64*     (2006.01)

(56) References Cited

OTHER PUBLICATIONS

Taran et al., "High-Throughput Screening of Enantioselective Catalysts by Immunoassay," Angew. Chem. Int. Ed. 2002, 41(1) 124-127 (Year: 2002).*
English abstract; Chinese Application with Publication No. CN1112563A.
Chinese Application with Publication No. CN1439643A.
Chinese Application with Publication No. CN101671365A.

* cited by examiner

```
Peak RetTime Type  Width     Area       Height      Area
 #   [min]        [min]     [mAU*s]     [mAU]        %
----|--------|----|--------|----------|------------|--------|
  1  11.855  VB   0.2496   1.36085e4   846.38763   96.2531
  2  20.141  BBA  0.3590    529.74707   22.97806    3.7469

Totals :                   1.41382e4   869.36569
```

```
Peak RetTime Type  Width     Area       Height      Area
 #   [min]        [min]     [mAU*s]     [mAU]        %
----|--------|----|--------|----------|------------|--------|
  1   9.389  BB   0.2109   1.67179e4  1242.99023   98.9050
  2  11.456  BB   0.2425    185.08586   11.83152    1.0950

Totals :                   1.69030e4  1254.82176
```

Signal 1: DAD1 A, Sig=215,4 Ref=360,100

| Peak # | RetTime [min] | Type | Width [min] | Area [mAU*s] | Height [mAU] | Area % |
|---|---|---|---|---|---|---|
| 1 | 14.729 | BB | 0.2629 | 68.90124 | 3.96143 | 0.4014 |
| 2 | 16.220 | BB | 0.2621 | 1.70977e4 | 1017.05078 | 99.5986 |

Totals :   1.71666e4   1021.01221

ASYMMETRICAL HYDROGENATION REACTION OF KETONIC ACID COMPOUND

The present application claims priority of Chinese application number 201410468805.9, filed to Chinese Patent Office on Sep. 15, 2014, titled "Asymmetrical hydrogenation reaction of an ∂-ketonic acid compound", the entire contents of which are hereby incorporated by reference.

FIELD OF INVENTION

The present invention relates to ligand chemistry technical field, specifically relates to the asymmetrical hydrogenation reaction of an ∂-ketonic acid compound.

BACKGROUND OF THE INVENTION

Rarely disclosure about the asymmetrical hydrogenation reaction of an ∂-ketonic acid compound. In the ligand field, the disclosure of the asymmetrical hydrogenation reaction of an ∂-ketonic acid compound by directly using an metal ligand complex also basically on an vacancy stage. The reasons through analyzing can be concluded as: the carboxyl group on the ∂-ketonic acid compound can coordinate with metal, in that way it will result the catalysts to be poisoned and spoiled, so the reaction yield is lowered. What's more, the two ∂ carbonyl groups one on the ∂-ketonic acid compound and the other on the carboxylic acid are nearly in coplanar position, there will result equal opportunities for chiral ligand catalysts to attack ∂-ketonic acid compound from two sides, of course, leads to lower enantioselectivity and reaction yield.

The following structure chiral spiro-pyridylamidophosphine ligand iridium complex are developed at the earliest by Nankai university.

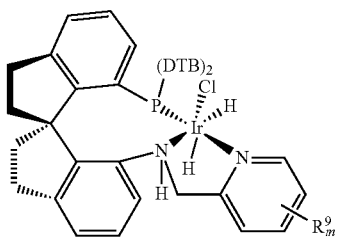

And it has been disclosed in Chinese application documents with the publication number CN102040625, the chiral spiro-pyridylamidophosphine ligand iridium complex used as a catalyst in the asymmetrical hydrogenation reaction of carbonyl compounds including aryl alkyl ketones, ketenes and keto esters. However, the chiral catalysts actually obtained a little bad catalytic result for keto esters compounds according to its Example 11 table 1 serial number 27.

Considering asymmetrical hydrogenation reaction technology are on an important position and are widely used in organic chemistry, it is necessary to overcome the defects of this technology in the application of ∂-ketonic acid compound. And it is also necessary to improve the asymmetrical hydrogenation reaction technology to form a new technical proposal to finally solve the problem which hardly or difficulty to catalytic ∂-ketonic acid compound.

SUMMARY OF THE INVENTION

To solve the technical problem of ∂-ketonic acid compound which are hardly or difficulty to carry out asymmetrical hydrogenation reaction technology, the present invention provides the following technical proposal:

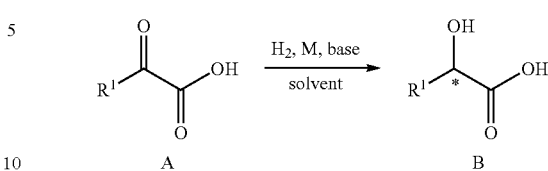

Wherein $R^1$ is a phenyl, a substituted phenyl, a naphthyl, a substituted naphthyl, a $C_1$-$C_6$ alkyl or aralkyl, the substitute is a $C_1$-$C_6$ alkyl, a $C_1$-$C_6$ alkoxy a halogen, the number of the substituents is 1-3.

Wherein, M can be the following structure chiral spiro-pyridylamidophosphine ligand iridium complex,

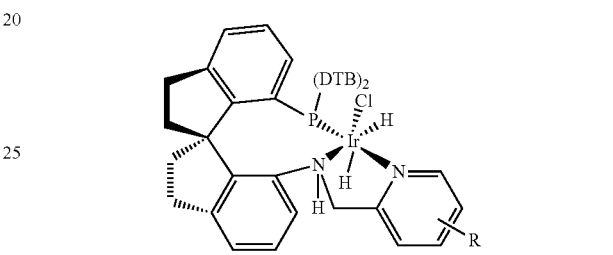

Wherein, R is hydrogen, 3-methyl, 4-$^t$Bu or 6-methyl.

The said base can be selected from sodium hydroxide, potassium hydroxide, sodium tert-butyl oxide, potassium tert-butyl oxide. The molar dosage ratio of the said base to the substrate A compound is (1.0~3):1, the preferred molar ratio is (1.001~1.5):1.

The said solvent can be selected from methanol, ethanol propanol, isopropanol, tetrahydrofuran, toluene, methyl tert-butyl ether, dioxane, DMF etc.

To be preferable, $R^1$ represents phenyl, substituted phenyl, naphthyl, substituted naphthyl.

Preferably, the present invention takes the following technical proposal: under the protection of nitrogen atmosphere, at a hydrogen pressure of 0.5-10 MPa, with a base dosage 1.0~3.0 molar equivalent, in the presence of organic solvent, ∂-ketonic acid compound is successfully formed into B compound in the catalytic of chiral spiro-pridylamidophosphine ligand iridium complex (M) with the molar dosage 0.00001~0.01 molar equivalent.

To be more preferable, under the protection of nitrogen atmosphere, were added into the inner hydrogenation tube substrate A, 1.0~3.0 molar equivalent (eq) base selected from sodium hydroxide, potassium hydroxide, sodium tert-butyl oxide or potassium tert-butyl oxide, chiral spiro-pyridylamidophosphine ligand compound (M) with the molar dosage 0.00001~0.01 molar equivalent (eq) and the solvent. The inner reaction tube was placed into the hydrogenation reactor at a hydrogen pressure of 0.5-10 MPa was filled. The reaction was stirred for 1-30 hours at a temperature of 10~90° C. to obtain B compound.

The technical proposal of the present invention can overcome the produced strong coordination effects between carboxyl group of the substrate and central metals through changing the base dosage, and successfully realize directly asymmetrical hydrogenation reaction of ∂-ketonic acid compound.

DETAILED EMBODIMENTS

Figure 1:
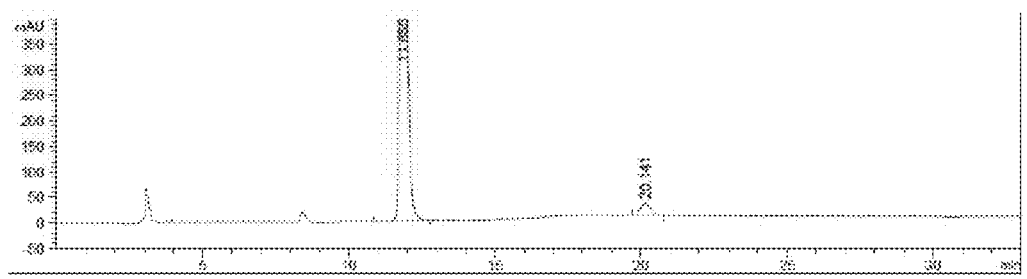
FIG. 1 illustrates the spectrum of High Performance Liquid Chromatography (HPLC) of the 3a compound prepared in accordance with Example 12 of the present invention.
Figure 2:
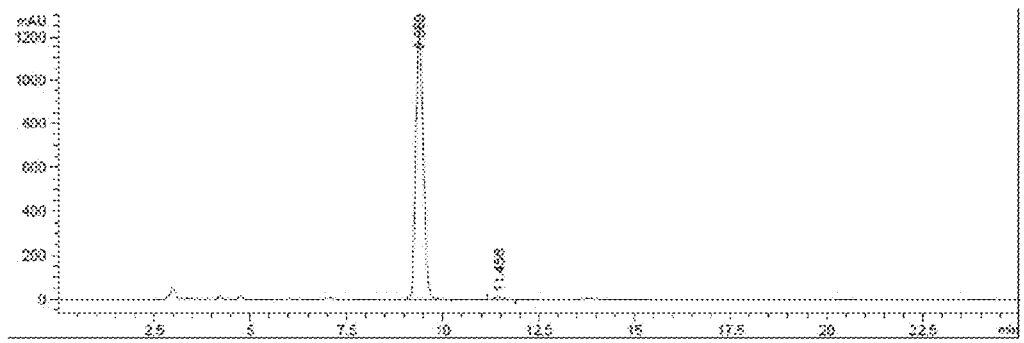
FIG. 2 illustrates the spectrum of High Performance Liquid Chromatography (HPLC) of the 3c compound prepared in accordance with Example 17 of the present invention.
Figure 3:
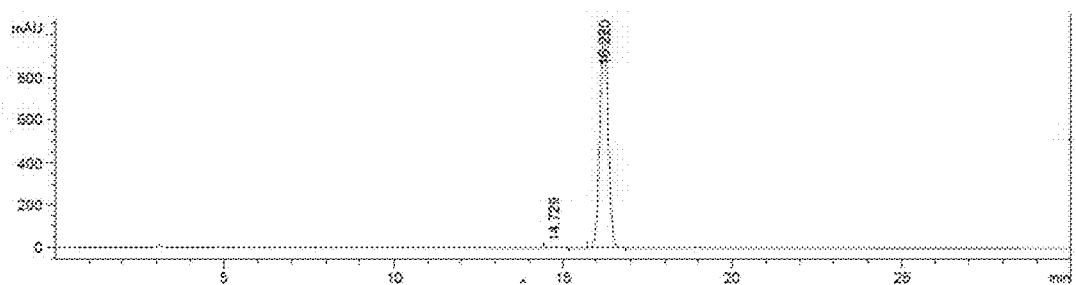
FIG. 3 illustrates the spectrum of High Performance Liquid Chromatography (HPLC) of the 3l compound prepared in accordance with Example 26 of the present invention.

In order to further understand the present invention, preferable embodiments of the present invention will be described by reference to the examples, but it should be appreciated that these descriptions are merely intended to further illustrate the features and advantages of the present invention, rather than limiting the claims of the invention.

HPLC analytical instrument and method
instrument model: Agilent 1200
chromatographic column: Chiracel OD-H, 4.6 mm×250 mm×5 μm
mobile phase A n-hexane
mobile phase B: isopropanol
flow velocity: 1.0 mL/min
column temperature: 35° C.
wave length: 210 nm
sample size: 5 μL

Example 1: Preparation of 2-hydroxyl-2-phenyl acetic acid

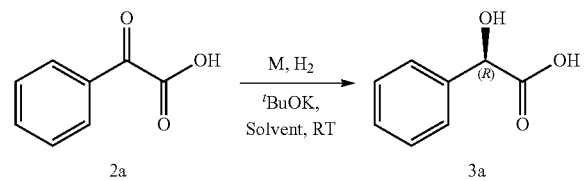

Under the protection of nitrogen atmosphere, to the inner hydrogenation tube (200 mL), were added substrate ∂-ketonic acid 2a (3 g, 20 mmol), potassium tert-butyl oxide (112 mg, 1 mmol), catalyst M (20 mg, 0.02 mmol, R=3-methyl) and solvent (50 mL). The inner reaction tube was placed into the hydrogenation reactor. After substitution by hydrogen, with hydrogen filled to a pressure of 15 atm, the reaction was stirred under the hydrogen pressure at room temperature for 24 hours. After the hydrogenation was finished, release hydrogen, and open the hydrogenation reactor. The reaction solution was filtered through a short silica gel column to remove the catalyst, and the conversion rate and yield of the reaction were analyzed by nuclear magnetic resonance (NMR). And the optical purity of the product was analyzed after derived to methyl ester compound. The results are listed as table 1.

The experimental results of Example 2-15 in the following table 1 were carried out according to or referred to the same method of the Example 1.

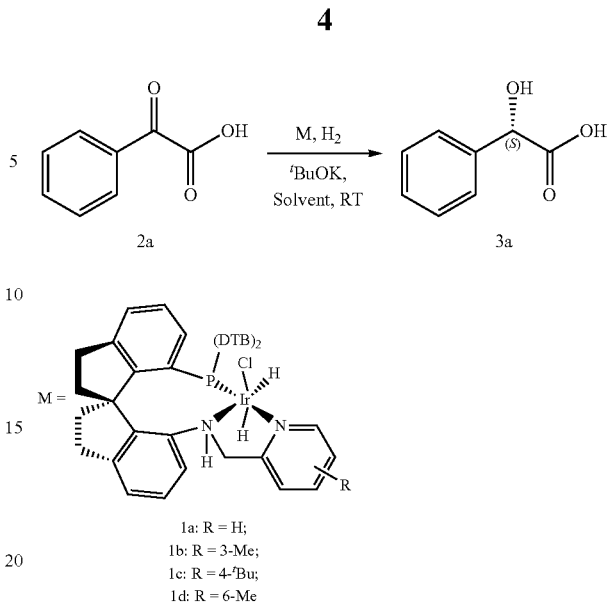

1a: R = H;
1b: R = 3-Me;
1c: R = 4-$^t$Bu;
1d: R = 6-Me

TABLE 1

| Example | M | B/S | $P_{H2}$ (atm) | Solvent | Time (h) | Conv. (%) | Ee (%) |
|---|---|---|---|---|---|---|---|
| 1 | 1b | 0.05 | 15 | EtOH | 24 | trace | not determing |
| 2 | 1b | 0.5 | 15 | EtOH | 24 | trace | not determing |
| 3 | 1b | 1.0 | 15 | EtOH | 10 | 100 | 87 (S) |
| 4 | 1b | 1.06 | 15 | EtOH | 2 | 100 | 87 (S) |
| 5 | 1b | 1.5 | 15 | EtOH | 2 | 100 | 87 (S) |
| 6 | 1b | 3 | 15 | EtOH | 2 | 100 | 85 (S) |
| 7 | 1b | 1.06 | 15 | MeOH | 21 | 92 | 78 (S) |
| 8 | 1b | 1.06 | 15 | $^i$PrOH | 20 | 100 | 87 (S) |
| 9 | 1b | 1.06 | 15 | $^n$PrOH | 2 | 100 | 88 (S) |
| 10 | 1b | 1.06 | 15 | $^n$BuOH | 2 | 100 | 89 (S) |
| 11 | 1a | 1.06 | 15 | $^n$BuOH | 3 | 100 | 85 (S) |
| 12 | 1c | 1.06 | 15 | $^n$BuOH | 1.5 | 100 | 96 (S) |
| 13 | 1d | 1.06 | 15 | $^n$BuOH | 2 | 100 | 83 (S) |
| 14 | 1c | 1.06 | 5 | $^n$BuOH | 8 | 100 | 91 (S) |
| 15 | 1c | 1.06 | 60 | $^n$BuOH | 1.5 | 100 | 92 (S) |

Wherein B/S represents the molar ratio of basic dosage and substrate ∂-ketonic acid dosage, conv. represents the conversion rate analyzed by nuclear magnetic resonance (NMR).

The experimental results of Example 16-30 in the following table 2 were carried out in the catalytic of 1c according to or referred to the same method of the Example 1.

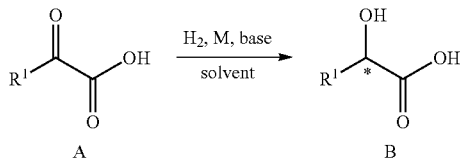

TABLE 2
| example | substrate | product | Reaction time (h) | yield (%) | Ee (%) |
|---|---|---|---|---|---|
| 16 | 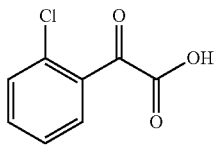 [SMILES: O=C(O)C(=O)c1ccccc1Cl] 2b | 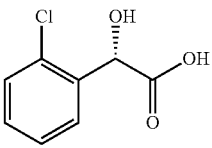 [SMILES: O=C(O)[C@@H](O)c1ccccc1Cl] 3b | 1 | 93 | 91 (S) |
| 17 | 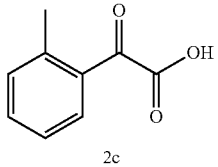 2c | 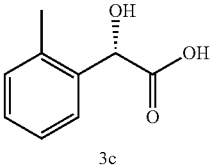 3c | 1 | 98 | 98 (S) |
| 18 | 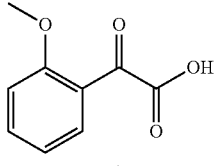 2d | 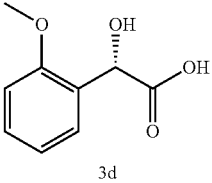 3d | 3 | 97 | 92 (S) |
| 19 | 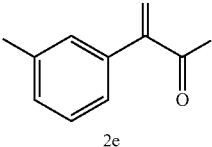 2e | 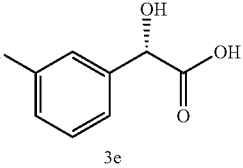 3e | 5 | 94 | 91 (S) |
| 20 | 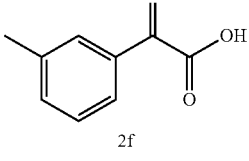 2f | 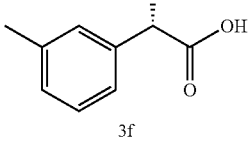 3f | 3 | 95 | 92 (S) |
| 21 | 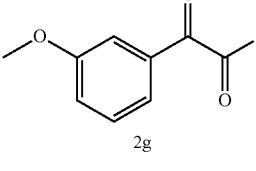 2g | 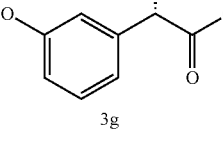 3g | 4 | 97 | 94 (S) |
| 22 | 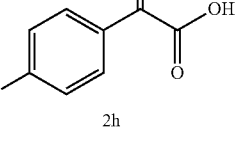 2h | 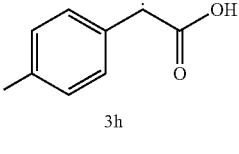 3h | 5 | 94 | 90 (S) |
| 23 | 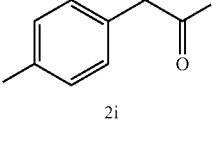 2i | 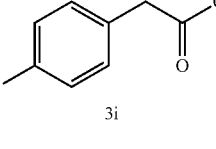 3i | 4 | 97 | 88 (S) |

TABLE 2-continued

| example | substrate | product | Reaction time (h) | yield (%) | Ee (%) |
|---|---|---|---|---|---|
| 24 | 2j | 3j | 4 | 97 | 90 (S) |
| 25 | 2k | 3k | 8 | 96 | 90 (S) |
| 26 | 2l | 3l | 1 | 98 | 99.2 (S) |
| 27 | 2m | 3m | 12 | 98 | 91 (S) |
| 28 | 2n | 3n | 2 | 95 | 82 (S) |
| 29 | 2o | 3o | 21 | 92 | 77 (R) |
| 30 | 2p | 3p | 1 | 96 | 56 (S) |

Example 31: Preparation of (R)-2-hydroxyl-2-(2-chlorin phenyl) acetic acid

S/C=50000 Carry out the highly conversion experiment in accordance with the same method disclosed in Example 1.

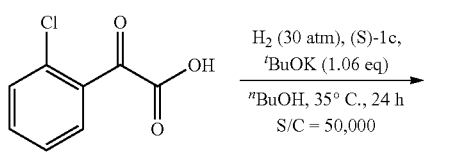

(R)-3b, 95% yield, 91% ee; product toluene through recrystallization: 80% yield, 99.1% ee Clopidogrel

Example 32: Preparation of (S)-2-hydroxyl-2-phenyl acetic acid

Under the protection of nitrogen atmosphere, to the inner hydrogenation tube (200 mL), were added substrate ∂-ketonic acid 2a (3 g, 20 mmol), potassium tert-butyl oxide (1.68 g, 30 mmol), catalyst 1c (20 mg, 0.02 mmol) and n-butanol (50 mL). The inner reaction tube was placed into the hydrogenation reactor. After substitution by hydrogen, with hydrogen filled to a pressure of 30 atm, the reaction was stirred under the hydrogen pressure at room temperature for 10 hours. After the hydrogenation was finished, release hydrogen and open the hydrogenation reactor. The reaction solution was filtered through a short silica gel column to remove the catalyst, and the conversion rate and yield of the reaction were analyzed by nuclear magnetic resonance (NMR). The conversion rate is 100%. And the optical purity of the product was analyzed after derived to methyl ester compound. The optical purity is 84% ee.

Example 33: Preparation of (S)-2-hydroxyl-2-(2-naphthyl) acetic acid

Under the protection of nitrogen atmosphere, to the inner hydrogenation tube (200 mL), were added substrate ∂-ketonic acid 2m (4 g, 20 mmol), potassium tert-butyl oxide (3.36 g, 30 mmol), catalyst 1b (20 mg, 0.02 mmol) and n-butanol (50 mL). The inner reaction tube was placed into the hydrogenation reactor. After substitution by hydrogen, with hydrogen filled to a pressure of 15 atm, the reaction was stirred under the hydrogen pressure at room temperature for 12 hours. After the hydrogenation was finished, release hydrogen, and open the hydrogenation reactor. The reaction solution was filtered through a short silica gel column to remove the catalyst, and the conversion rate and yield of the reaction were analyzed by nuclear magnetic resonance (NMR). The conversion rate is 100%. And the optical purity of the product was analyzed after derived to methyl ester compound. The optical purity is 95% ee.

Example 34: Preparation of (R)-2-hydroxyl-3,3-dimethyl butanoic acid

Under the protection of nitrogen atmosphere, to the inner hydrogenation tube (200 mL), were added substrate ∂-ketonic acid 2o (2.6 g, 20 mmol) potassium tert-butyl oxide (3.36 g, 30 mmol), catalyst 1b (40 mg, 0.04 mmol) and n-butanol (50 mL). The inner reaction tube was placed into the hydrogenation reactor. After substitution by hydrogen, with hydrogen filled to a pressure of 15 atm, the reaction was stirred under the hydrogen pressure at room temperature for 24 hours. After the hydrogenation was finished, release hydrogen, and open the hydrogenation reactor. The reaction solution was filtered through a short silica gel column to remove the catalyst, and the conversion rate and yield of the reaction were analyzed by nuclear magnetic resonance (NMR). The conversion rate is 100%. And the optical purity of the product was analyzed after derived to benzyl ester compound. The optical purity is 85% ee.

Although fully description has been made for the present application in combing the specific Examples, it is apparent

The invention claimed is:

1. A preparation method of the structure of formula B,

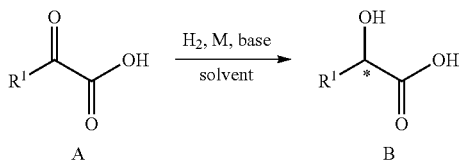

Wherein $R^1$ is a phenyl, a substituted phenyl, a naphthyl, a substituted naphthyl, a $C_1$-$C_6$ alkyl or aralkyl, the substitute is a $C_1$-$C_6$ alkyl, a $C_1$-$C_6$ alkoxy, a halogen, the number of the substituents is 1-3

Wherein M is the following structure chiral spiro-pyridylamidophosphine ligand iridium complex:

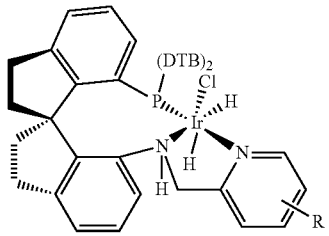

Wherein R is hydrogen, 3-methyl, 4-$^t$Bu or 6-methyl,

The said base is selected from sodium hydroxide, potassium hydroxide, sodium tert-butyl oxide or potassium test-butyl oxide, The molar dosage ratio of the said base to the substrate A compound is (1.0~3):1.

2. The preparation method according to claim 1, wherein, the molar dosage ratio of the said base to the substrate A compound is (1.001~1.5):1.

3. The preparation method according to claim 1, wherein, $R^1$ is a phenyl, a substituted phenyl, a naphthyl or a substituted naphthyl.

4. The preparation method according to claim 1, wherein, R is 4-$^t$Bu.

5. The preparation method according to claim 1, wherein, the said base is sodium hydroxide or potassium hydroxide.

6. The preparation method according to any claims of 1, 3, 4 or 5, wherein, under the protection of nitrogen atmosphere, at a hydrogen pressure of 0.5-10 MPa, with a base dosage 1.0~3.0 molar equivalent, in the presence of organic solvent, ∂-ketonic acid compound is formed into B compound in the catalytic of chiral spiro-pyridylamidophosphine ligand iridium complex (M) with the molar dosage 0.00001~0.01 molar equivalent.

7. The preparation method according to any claims of 1, 3, 4 or 5, wherein, under the protection of nitrogen atmosphere, were added into the inner hydrogenation tube substrate A, 1.0~3.0 molar equivalent base, chiral spiro-pyridylamidophosphine ligand iridium complex (M) with the molar dosage 0.00001~0.01 molar equivalent and the solvent; The inner reaction tube was placed into the hydrogenation reactor at a hydrogen pressure of 0.5-10 MPa was filled; The reaction was stirred for 1-30 hours at a temperature of 10~90° C. to obtain B compound; the base selected from sodium hydroxide, potassium hydroxide, sodium tert-butyl oxide or potassium tert-butyl oxide.

8. The preparation method according to claim 1, wherein, the said solvent is selected from methanol, ethanol, propanol isopropanol, tetrahydrofuran, toluene, methyl tert-butyl ether, dioxane or DMF.

* * * * *